(12) United States Patent
Gaglani et al.

(10) Patent No.: US 7,323,044 B1
(45) Date of Patent: Jan. 29, 2008

(54) BIOCIDAL COMPOSITIONS

(75) Inventors: Kamlesh Gaglani, Belle Mead, NJ (US); Gordon Thakkar, Edison, NJ (US)

(73) Assignee: Troy Corporation, Florham Park, NJ (US)

( * ) Notice: Subject to any disclaimer, the term of this patent is extended or adjusted under 35 U.S.C. 154(b) by 0 days.

(21) Appl. No.: 11/656,210

(22) Filed: Jan. 22, 2007

(51) Int. Cl.
*A01N 55/02* (2006.01)
*A01N 25/02* (2006.01)
*A01N 43/16* (2006.01)

(52) U.S. Cl. .................... 106/18; 106/15.05; 514/185; 514/504

(58) Field of Classification Search ............ 106/15.05, 106/18; 514/504, 185
See application file for complete search history.

(56) References Cited

U.S. PATENT DOCUMENTS

| | | | |
|---|---|---|---|
| 2,678,935 A | 5/1954 | Sundberg et al. |
| 3,288,674 A | 11/1966 | Yeager |
| 3,312,542 A | 4/1967 | Kitzke et al. |
| RE29,409 E | 9/1977 | Yeager |
| 4,115,415 A | 9/1978 | Yoshihara et al. |
| 4,637,887 A | 1/1987 | Worschech et al. |
| 4,663,077 A | 5/1987 | Rei et al. |
| 4,681,900 A | 7/1987 | Iwasaki |
| 4,683,080 A | 7/1987 | Rei et al. |
| 4,849,470 A | * | 7/1989 | Murphy ...................... 524/714 |
| 5,102,657 A | | 4/1992 | Rei et al. |
| 5,319,000 A | | 6/1994 | O'Connor et al. |
| 5,399,728 A | | 3/1995 | Cooper |
| 5,405,610 A | | 4/1995 | Rei et al. |
| 5,488,065 A | | 1/1996 | Roth |
| 5,629,342 A | | 5/1997 | Roth |
| 5,639,803 A | | 6/1997 | Anderson et al. |
| 5,827,522 A | | 10/1998 | Nowak |
| 5,929,132 A | | 7/1999 | Hani et al. |
| 6,265,373 B1 | | 7/2001 | Oses et al. |
| 6,544,938 B1 | | 4/2003 | Yarovoy et al. |
| 2001/0026803 A1 | | 10/2001 | Tebbe et al. |

* cited by examiner

*Primary Examiner*—Anthony J. Green
(74) *Attorney, Agent, or Firm*—Robert A. Yesukevich

(57) ABSTRACT

The invention provides co-solvents for preparing clear solutions of a biocidal agent known as 10, 10'-oxybisphenoxarsine (OBPA). The clear solutions are stable over a relatively broad range of temperatures and have very low Volatile Organic Carbon (VOC) content. They can be included in master batches for the manufacture of plastic materials, such as flexible PVC. The co-solvents of this invention have very low VOC values, do not have troublesome odors, do not cause significant irritation during the high temperature plastic manufacturing process, and are miscible in a range of useful concentrations with plasticizers presently employed by plastics manufacturers. The use of castor oil and/or modified castor oils such as glyceryl ricinoleate, dehydrated castor oil, and certain alkoxylated castor oils as a co-solvent to increase the dissolvable concentration of OBPA, alone or in solution with a plasticizer, was not known or expected.

12 Claims, No Drawings

BIOCIDAL COMPOSITIONS

BACKGROUND OF THE INVENTION

1. Field of the Invention

The present invention relates to novel vehicles for introducing one or more compounds of the phenoxarsine family of biocides into starting mixtures which can be utilized in manufacturing processes for plastic materials.

2. Description of Related Art 10,10'-oxybisphenoxarsine (hereinafter referred to as "OBPA") is a biocidal agent known to be suitable for use in plastic materials such as, for example, flexible polyvinyl chloride (hereinafter referred to as "flexible PVC"). In the course of manufacturing the plastic material, OPBA is typically incorporated via a solution including OBPA as a solute and one or more solvents. The solvent may subsequently perform a beneficial role, such as that of plasticizer, in the manufacturing process. At a minimum, the solvent should not detrimentally affect the properties of the finished plastic material.

Using a more concentrated OBPA solution rather than a less concentrated OBPA solution tends to reduce shipping costs and storage costs. While the plastics manufacturing industry generally utilizes solutions including in the range of about 1 to about 3 wt % OBPA, solutions including 5 wt % OBPA or more are desirable.

Because the solubility of OBPA in those plasticizers currently favored for manufacturing flexible PVC is less than 1 wt %, it has long been industry practice to dissolve OBPA in a combination of solvents, known as co-solvents, so that a more concentrated solution of the OBPA can be supplied to the flexible PVC manufacturer. The use of appropriate co-solvents tends to ensure that the OBPA dissolves completely, and remains dissolved, in the OBPA solution.

Representative plasticizers for manufacturing plastics include diisodecyl phthalate, 2-di (2-ethylhexyl) phthalate, polypropylene glycol, butylbenzyl phthalate, and epoxidized soybean oil, among others. For manufacturing flexible PVC, dioctyl diphthalate, diisononyl phthalate, diisodecyl phthalate and butyl benzyl phthalate are commonly employed as plasticizers. While these traditional plasticizers are utilized as solvents or co-solvents for OBPA, none has proven entirely satisfactory.

A typical OBPA solution includes an alcohol as a first co-solvent and a plasticizer as a second co-solvent. More specifically, an OBPA supplier may provide a flexible PVC manufacturer with a solution of 1 to 5 wt % OBPA, 8 to 20 wt % of an alcohol and 75 to 90 wt % of a plasticizer. Such an OBPA solution is routinely exposed to extremes of heat and cold during transportation and storage. Despite these temperature extremes, the OBPA solution should not exhibit any evidence of precipitation, phase separation or clouding. To the contrary, the OBPA solution should remain in the form of a clear, homogenous liquid until such time as it may be added to the flexible PVC manufacturing process during a compounding operation, which may be a "plastisol blending operation" or a "dry blending operation," among others.

The compounding operation traditionally incorporates performance additives into flexible PVC in order to increase its usefulness. The additives may be, for example, plasticizers to increase the flexibility of the finished product, heat stabilizers to prevent degradation and discoloration of the PVC at the elevated temperatures required for processing, lubricants to improve the flow of the molten PVC and to prevent its sticking to metal processing surfaces, fillers to increase the bulk and lower the cost of the final material, and pigments to produce the desired color, among others.

In the compounding operation, the OBPA solution and the performance additives are mixed with resins and stirred at a temperature in the range of about 93-107° C., which range is below the fusion temperature of the resins. In the case of dry blending, resin particles imbibe the liquid and the result is a powder barely distinguishable in appearance from the original resin. In the case of plastisol blending, the result is a liquid. In either dry blending or plastisol blending, the resulting powder or liquid may be subsequently stored or fed directly to fabricating equipment where relatively high temperatures produce a fused compound in the manufacturing process.

Over the years, a number of co-solvents have been proposed for dissolving OBPA. For example U.S. Pat. No. 3,288,674, issued to Yeager, describes the use of solvents which are phenols, such as nonylphenol. Other patents mention the use of aliphatic alcohols as well as certain phosphites and phosphonates, such as tris(dipropyleneglycyl)phosphate.

Several of these co-solvents have been commercially successful, but none is entirely satisfactory. For example, isodecyl alcohol, which is currently used as a commercial co-solvent, is associated with irritation to human beings during the high temperature processing of flexible PVC.

U.S. Pat. No. 5,488,065, issued to Roth, describes aromatic alcohols, such as benzyl alcohol, as co-solvents which are less irritating to humans. Reportedly, benzyl alcohol produces less odor and irritation, as compared to nonyl phenol and isodecyl alcohol. However, benzyl alcohol cannot be considered a final answer because it does not completely eliminate irritation to humans, and because it contains an undesirably high amount of volatile organic carbon (hereinafter referred to as "VOC").

The use of VOC's in the United States of America is regulated by both federal and state governments. While the various governmental entities sometimes adopt different definitions, the U.S. Code of Federal Regulations defines VOC in 40 CFR Part 51.100(s) as "any compound of carbon, excluding carbon monoxide, carbon dioxide, carbonic acid, metallic carbides or carbonates, and ammonium carbonate, which participates in atmospheric photochemical reactions" and is not specifically exempted or exempted by demonstrated performance under certain standardized test conditions. In order to facilitate compliance, the plastics manufacturing industry is likely to welcome alternative co-solvents which perform well and are not classified as VOC's.

Each of the above-described vehicles or solvents has one or more disadvantages or deficiencies which make them less than ideal as a vehicle for OBPA. Many contain undesirable VOC's. Some have troublesome odors, low dissolving capacity at room temperature, relatively high viscosity, unsatisfactory miscibility with the plasticizers usually used in the plastic materials industry, unsuitable toxicological properties and the like. Accordingly, a need exists for an improved solvent or co-solvent for introducing OBPA into a manufacturing process for plastic materials.

SUMMARY OF THE INVENTION

It has now been discovered that clear solutions of a biocidal agent are prepared by dissolving OBPA in a suitable mixture of castor oil and/or a castor oil derivative and optionally a plasticizer, and that this clear solution can be included in master batches for the manufacture of plastic materials. These solutions are especially useful in the manufacture of flexible PVC. The use of castor oil and/or a castor oil derivative as a co-solvent to increase the dissolvable concentration of OBPA in solution was not known or expected.

It is the surprising finding of this invention that castor oil and modified castor oils such as partially dehydrated castor oil, certain alkoxylated castor oils, and the like can be used as a solvent or co-solvent for OBPA. The co-solvents of this invention have very low VOC values, do not have troublesome odors, do not cause significant irritation during the high temperature plastic manufacturing process, and are miscible in a range of useful concentrations with the plasticizers presently employed by plastics manufacturers. The co-solvents of this invention maintain OBPA in solution with the plasticizer at the temperatures required for storage, transportation and the plastic manufacturing process.

In one aspect, the invention is a novel biocidal composition for blending in a process for manufacturing a plastic material. The composition comprises a biocidal agent and a solvent selected from the group consisting of castor oil, alkoxylated castor oil having less than about 200 mols of alkoxyl per mol of glyceride, dehydrated castor oil, glyceryl ricinoleate, alkoxyolated glyceryl ricinoleate having less than about 200 mols of alkoxyl per mol of glyceride, dehydrated glyceryl ricinoleate, and mixtures thereof. The biocidal agent is most preferably OBPA. The composition may optionally include a plasticizer and various conventional additives for manufacturing plastic materials. Preferably, the composition has a VOC of less than about 10 grams per liter, more preferably less than about 1 gram per liter.

In another aspect the invention is a biocidal composition for blending with a plastisol. The biocidal composition includes OBPA and a mixture of triglycerides of fatty acids. The esterified ricinoleic acid content of the triglycerides mixture is about 90 wt % of the total esterified fatty acid content of the triglycerides mixture.

In yet another aspect, the invention is a biocidal composition for manufacturing a plastic material, comprising OBPA and a dehydrated glyceryl ricinoleate, which is manufactured from glyceryl ricinoleate by a dehydration process and has an iodine value in the range of about 90 to about 180.

In still another aspect, the invention is a biocidal composition, which composition comprises OBPA and an alkoxylated castor oil, which has less than about 200 mols of alkoxyl per mol of glyceride and includes a mixture of ricinoleic acid triesters of alkoxylated glycerol.

DETAILED DESCRIPTION OF PREFERRED EMBODIMENTS OF THE INVENTION

Applicants have discovered a composition which is suitable for introducing OBPA into plastics manufacturing processes in the form of a clear solution, and is stable over a relatively broad temperature range. The composition has very low VOC and is especially useful for manufacturing flexible PVC.

The inventive composition is prepared by combining OBPA with an effective amount of castor oil, alkoxylated castor oil having less than about 200 mols of alkoxyl per mol of glyceride, dehydrated castor oil, glyceryl ricinoleate, alkoxyolated glyceryl ricinoleate having less than about 200 mols of alkoxyl per mol of glyceride, dehydrated glyceryl ricinoleate or mixtures thereof (referred to hereinafter collectively as "castor oil based co-solvent") and, optionally, a plasticizer. The plasticizer can be the same as or different from any of the components present in the castor oil based co-solvent. These components, and the optional plasticizer (if present), are normally rendered transparent by maintaining the composition at a temperature of about 100° C. The hot solution can then be cooled to room temperature with essentially no observable precipitation, phase separation or clouding. By way of comparison, OBPA is soluble in commercially practical concentrations at 100° C. in a number of solvents including some vegetable oils, but precipitates out of solution with the unsuccessful co-solvents when cooled to room temperature.

"Effective amount of castor oil based co-solvent" means an amount of castor oil based co-solvent sufficient to prevent OPBA from precipitating from the solution. This will depend, of course, primarily on the concentration of OBPA in the solution. It may also depend on whether other adjuvants are added to the solution, whether other co-solvents are used and, to some degree, on the minimum temperature at which the solution is or has been maintained.

As a general rule, OBPA solutions which are transported or stored at outdoor conditions, without the benefit of dedicated heating or cooling equipment, may be exposed to temperatures in the range of about −13° C. to about 30° C. We have found that at least about 8 grams of a castor oil based co-solvent are required to keep 1 gram of OBPA in solution with plasticizers now commercially employed (e.g., diisodecyl phthalate) for the fabrication of flexible PVC throughout this temperature range. For OBPA solutions which will be transported or stored at outdoor conditions, we prefer that the weight ratio of OBPA to the solvent is about 0.12 or less in the present invention, more preferably in the range of about 0.083 to about 0.12, and most preferably about 0.10. For OBPA solutions which will be temperature-controlled during shipment and storage, the invention can be successfully practiced over a broader range of OBPA to solvent weight ratio.

Extending this finding to commercial solutions containing 2 wt % or 5 wt % OBPA, the amount of co-solvent required to maintain such commercially desirable amounts of OBPA in solution should be about 16 wt % and about 40 wt % respectively. To be on the safe side, it is preferred to use about 10 g of castor oil based co-solvent for every gram of OBPA.

Consequently, a 2 wt % OBPA solution would preferably contain about 2 wt % OBPA, about 20 wt % castor oil based co-solvent and about 78 wt % plasticizer; and a 5 wt % OBPA solution would preferably contain about 5 wt % OBPA, about 50 wt % castor oil based co-solvent and about 45 wt % plasticizer. Solutions containing as little as about 0.5 wt % OBPA and 4 wt % castor oil based co-1-solvent to solutions that contain as much as 11 wt % OBPA and 88 wt % castor oil based co-solvent are contemplated.

Solutions including in the range of about 0.5 to about 6 wt % OBPA, about 5 to about 60 wt % of a castor oil based co-solvent selected from the group consisting of castor oil, alkoxylated castor oil having less than about 200 mols of alkoxyl per mol of glyceride, dehydrated castor oil, glyceryl ricinoleate, alkoxyolated glyceryl ricinoleate having less than about 200 mols of alkoxyl per mol of glyceride, dehydrated glyceryl ricinoleate, and mixtures thereof, and about 34 to about 94 wt % of a plasticizer are preferred. Solutions including in the range of about 1.5 to about 2.5 wt % 10, 10'-oxybisphenoxarsine, about 15 to about 25 wt % of the castor oil based co-solvent, and about 72 to about 82 wt % of the plasticizer are especially preferred. Solutions including in the range of about 4.5 to 5.5 wt % OBPA, about 45 to about 55 wt % of the castor oil based co-solvent, and about 39 to about 50 wt % of the plasticizer are also especially preferred.

"Castor oil" means a mixture including triglycerides of fatty acids, with the esterified ricinoleic acid content being approximately 90 wt % of the total esterified fatty acid content of the mixture. Other esterified fatty acids which are typically present in the mixture include esterified linoleic acid (about 4.2 wt %), esterified oleic acid (about 3.0 wt %), esterified palmitic acid (about 1.0 wt %) and esterified stearic acid (about 1.0 wt %). Castor oil is normally obtained as an extract from the seed of the castor bean plant, which has the botanical name *Ricinus communis*.

"Alkoxylated castor oil" means an essentially acyclic product manufactured from castor oil by a condensation process with an alkylene oxide such as ethylene oxide or propylene oxide, or by a condensation process with a polyalkylene glycol such as polyethylene glycol or polypropylene glycol. Alkoxylated castor oil may include a mixture of ricinoleic acid triesters of alkoxylated glycerol with relatively small amounts of ricinoleic acid mono- and di-esters of alkoxylated glycerol, free ricinoleic acid and free glycols.

"Glyceryl ricinoleate" means a triglyceride of the formula:

"Alkoxyolated glyceryl ricinoleate" means a compound of either Formula A or Formula B, as shown below:

Formula A

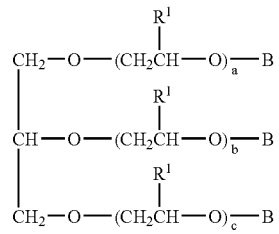

wherein each of a, b, and c is an integer in the range of 1 to about 80, the sum of a, b, and c is an integer in the range of 1 to less than about 200, R1 is H or CH3, and B is H or

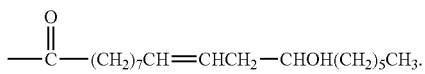

Formula B

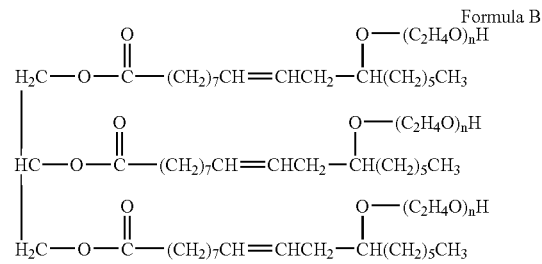

wherein n is an integer in the range of 1 to less than about 200.

In addition, glycerides of the present invention may be a mixture of mono-, di- and triesters of glycerol as described above, having a statistical distribution of less than about 200 alkoxyl mols per mol of glyceride.

"Dehydrated castor oil" means a product manufactured from castor oil by a dehydration process which removes at least some hydroxyl groups and hydrogens from esterified ricinoleic acid chains in the castor oil. It is preferred that dehydrated castor oil used in the present invention have an iodine value in the range of about 90 to about 180, more

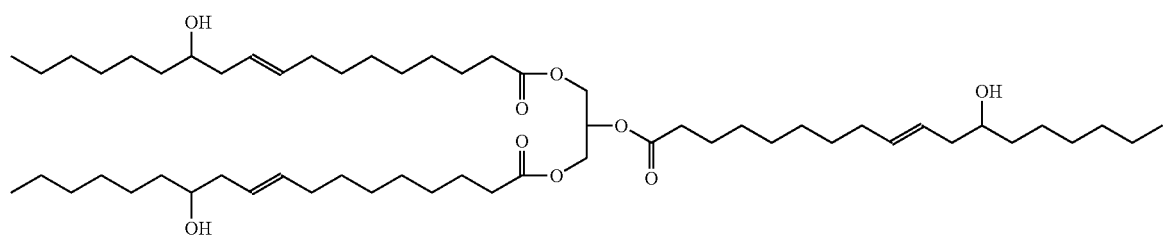

preferably about 100 to about 160, and most preferably about 125 to about 145, as measured by the standardized method known as USP 28.

"Dehydrated glyceryl ricinoleate" means a mixture having an iodine value in the range of about 90 to about 180, more preferably about 100 to about 160, and most preferably about 125 to about 145, as measured by the standardized method known as USP 28, which mixture includes a significant amount of a triglyceride of the formula:

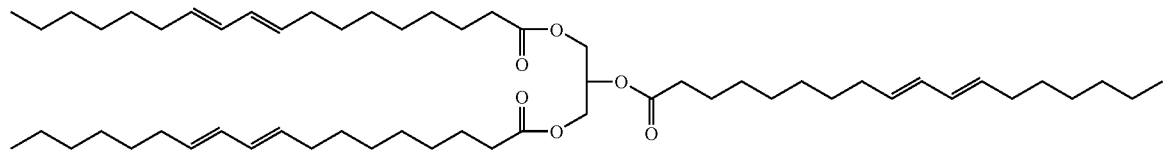

The selection of plasticizers suitable for the present invention is within the expertise of persons skilled in plastic products manufacturing and process design. It is expected but not a requirement that the plasticizer for the present invention will be the one, or a plasticizer compatible with the one, used in the plastic manufacturing process. The plasticizer for the present invention may be the same, or different from, any of the components present in the castor oil based co-solvent.

Esters of polybasic acids (such as phthalic acid, adipic acid, trimellitic acid, and sebacic acid) with monovalent alcohols, such as ethylhexyl alcohol, isoheptyl alcohol, isodecyl alcohol, isotridecyl alcohol, having molecular weights of about 250 to about 500 daltons are commonly used plasticizers for manufacturing plastic. Other commonly used plasticizers for manufacturing plastic are polyesters made from glycols with dibasic acids having molecular weights of about 600 to about 1200 daltons.

Also reported as suitable plasticizers for manufacturing plastic are epoxidated vegetable oils, such as soya epoxide, castor oil epoxide and the like, and phosphoric acid esters, such as tricresyl phosphate, tri-2-ethylhexyl phosphate and the like. Phthalates are among the most widely used commercial plasticizers at present, especially for the manufacture of flexible PVC.

For use in the present invention, plasticizers which are esters of polybasic acids and have molecular weights of about 250 to about 500 daltons are preferred. Preferably, the plasticizer for use in the present invention is selected from the group consisting of diisononyl phthalate, diisodecyl phthalate, butylbenzyl phthalate, linear phthalate, epoxidized soybean oil, and mixtures thereof. "Linear phthalate" means an aromatic compound which can be produced by the reaction of a linear alcohol with phthalic anhydride.

OBPA is especially preferred for use as a microbiocidal agent in the present invention. "Microbe" means a minute life form such as, for example, a bacterium, fungus, mushroom, mold, smut, rust, or yeast.

Plastic materials in which OBPA can be incorporated by the compositions and methods of the present invention include flexible PVC formulations and blends of flexible PVC formulations with acetate co-polymers, synthetic rubbers and polyurethanes. The OBPA solutions of the present invention can be utilized for manufacturing any thermopolastic polymer of which the principal constituent is vinyl chloride. These polymers include homopolymers of vinyl chloride which have been obtained by emulsion, suspension and/or mass polymerization, as well as copolymers containing at least 50 wt % vinyl chloride and another polymerizable monomer, such as vinyl ester (particularly vinyl acetate), methacrylate (particularly methyl methacrylate and butyl methacrylate), fumaric acid ester, butadiene and vinylidene chloride. These polymers may be after-chlorinated.

Flexible PVC formulations are the preferred synthetic material to which this invention pertains. A further aspect of the present invention is concerned with a synthetic material, such as a flexible PVC, which has been manufactured using OBPA in the presence of a co-solvent of the present invention.

The present invention is also a method for the manufacture of a biocidal mixture or of a mixture suitable for the biocidal finishing of synthetic materials such as flexible PVC, which method comprises dissolving OBPA in a castor oil based co-solvent. A plasticizer may be included in the mixture.

Additionally, the present invention is concerned with a process for the manufacture of a synthetic material, such as a flexible PVC material, which process comprises dissolving OBPA in a castor oil based co-solvent and a plasticizer, and using the resulting mixture in the manufacture of synthetic plastic materials. The plasticizer and/or the resulting mixture may optionally include other plasticizers, UV absorbers, pigments, heat stabilizers, lubricants, and antioxidants.

EXAMPLE 1

A number of materials are subjected to the following procedure to determine which, if any, might be suitable as co-solvents for OBPA and diisodecyl phthalate.

In each procedure, a mixture is prepared by combining 5.0 g of 10, 10'-oxybisphenoxarsine with 45.0 g of diisodecyl phthalate and 50 g of a material of interest. The mixture is heated to a temperature in the range of 90-100° C. with stirring until it appears to be a single, clear liquid phase. The mixture is permitted to cool to room temperature (in the range of 22-25° C.) and samples of the cooled mixture are taken and stored for five days at room temperature, in a refrigerator for five days at 4° C. and in a freezer for five days at −13° C. The samples are observed for any evidence of precipitation, such as settling or clouding. Data is presented in Table I.

TABLE I

Physical Stability of 10,10'-oxybisphenoxarsine in Various Solutions

| Material of Interest | Of Invention or For Comparison | Room Temperature | Refrigerator | Freezer |
|---|---|---|---|---|
| Castor Oil[1] | Invention | CLEAR | CLEAR | CLEAR |
| Linseed Oil | Comparison | Precipitate[2] | Precipitate | Precipitate |

TABLE I-continued

Physical Stability of 10,10'-oxybisphenoxarsine in Various Solutions

| Material of Interest | Of Invention or For Comparison | Room Temperature | Refrigerator | Freezer |
|---|---|---|---|---|
| Soybean Oil | Comparison | Precipitate | Precipitate | Precipitate |
| Corn Oil | Comparison | Precipitate | Precipitate | Precipitate |
| Canola Oil | Comparison | Precipitate | Precipitate | Precipitate |
| ESO[3] | Comparison | CLEAR | CLEAR | Precipitate |
| Olive Oil | Comparison | Precipitate | Precipitate | Precipitate |
| Pine Oil[7] | Comparison | Precipitate[4] | Precipitate | Precipitate |
| Mineral Oil | Comparison | Precipitate | Precipitate | Precipitate |
| Tufflo Oil | Comparison | Precipitate | Precipitate | Precipitate |
| DCO[5] | Invention | CLEAR | CLEAR | CLEAR |
| IDA[6,7] | Comparison | CLEAR | CLEAR | CLEAR |

Legend:
[1] Because Castor Oil exhibits relatively low volatility at room temperature, it is unlikely to be classified as a VOC. Castor Oil USP of Lot 2-308 is obtained commercially from White, Home and Clark Co., Inc. of Newark, New Jersey and used in this procedure. Iodine Value for this Lot is reportedly 84.9.
[2] "Precipitate" means a solid precipitate is observed.
[3] ESO means Epoxidized Soybean Oil.
[4] Solution is clear initially and forms precipitate on standing.
[5] Dehydrated Castor Oil is obtained commercially from White, Home and Clark Co., Inc. of Newark, New Jersey under a general specification for Iodine Value of 125-145 by USP method.
[6] IDA means Isodecyl Alcohol, which is a commercially used solvent and plasticizer.
[7] Pine Oil and IDA are each known to have a relatively high VOC content.

The data in Table I indicates that specified solutions of 10, 10'-oxybisphenoxarsine, diisodecyl phthalate, and either castor oil or dehydrated castor oil are physically stable over a relatively broad range of temperature.

EXAMPLE 2

The procedure described above in Example 1 is performed with ethoxylated castor oils as the respective materials of interest. The ethoxylated castor oils are commercially supplied by Rhodia of Cranbury, N.J. under the trade names Alkamus EL-620 and Alkamus EL-985 and are specified as a PEG-30 derivative of castor oil and a PEG-200 derivative of castor oil, respectively. Data is observed and recorded below in Table II.

TABLE II

10,10'-oxybisphenoxarsine, Diisodecyl Phthalate and Ethoxylated Castor Oil

| Material of Interest | Of Invention or For Comparison | Room Temperature | Refrigerator | Freezer |
|---|---|---|---|---|
| Alkamuls EL-620 (a PEG-30 derivative of Castor Oil) | Invention | CLEAR | CLEAR | CLEAR |
| Alkamuls EL-985 (a PEG-200 derivative of Castor Oil) | Comparison | Precipitate | Not Applicable | Not Applicable |

The data in Table II indicates that a solution consisting of 5 wt % 10, 1'-oxybisphenarsazine, 45 wt % diisodecyl phthalate and 50 wt % ethoxylated castor oil derived from a polyethylene glycol of nominally about 30 ethylene oxide units is physically stable over a relatively broad range of temperature.

EXAMPLE 3

VOC values of a castor oil solution of the invention and of two previously known commercial solutions are determined using the following procedure. A sample of the solution is accurately weighed on an analytical balance scale. The sample is maintained in an oven at 105° C., cooled to room temperature and weighed on the analytical balance. The specific gravity of the solution of interest is measured. The difference in weight is reported as VOC on the basis of one liter of the solution of interest. The data is shown below in Table III.

TABLE III

VOC for Solutions including Biocide and Plasticizer

| | Of Invention or For Comparison | OBPA Biocide (wt %) | Diisodecyl Phthalate Plasticizer (wt %) | Solvent (wt %) | Observed VOC (g/l) |
|---|---|---|---|---|---|
| Castor Oil Solution | Invention | 5.0 | 45 | Castor Oil 50 | 0 |
| Benzyl Alcohol Solution | Comparison | 5.0 | 75 | Benzyl Alcohol 20 | 215 |
| Isodecyl Alcohol Solution | Comparison | 5.0 | 75 | Isodecyl Alcohol 20 | 204 |

The data in Table III indicates that a castor oil solution of the invention has very low VOC.

The above Examples are not intended to limit the present invention in any way. The present invention is defined by the appended claims.

We claim as our invention:

1. A biocidal composition for manufacturing a plastic material, which composition comprises:
   about 1.5 to about 5.5 wt % 10,10'-oxybisphenoxarsine, and
   a solvent selected from the group consisting of castor oil, alkoxylated castor oil having less than about 200 mols of alkoxyl per mol of glyceride, glyceryl ricinoleate, alkoxylated glyceryl ricinoleate having less than about 200 mols of alkoxyl per mol of glyceride, and mixtures thereof;
   which composition includes less than about 10 grams per liter of VOC; and
   which composition is a clear, homogeneous solution throughout the temperature range of about negative 13 to about 30 degrees Centigrade.

2. The composition of claim 1, in which the solvent is selected from the group consisting of alkoxylated castor oil having less than about 200 mols of alkoxyl per mol of glyceride, alkoxylated glyceryl ricinoleate having less than about 200 mols of alkoxyl per mol of glyceride, and mixtures thereof.

3. The composition of claim 1, in which the solvent is castor oil.

4. The composition of claim 1, in which a major component of the solvent is glyceryl ricinoleate.

5. The composition of claim 1, in which a weight ratio of 10, 10'-oxybisphenoxarsine to the solvent is about 0.12 or less.

6. The composition of claim 5, in which
   a) the weight ratio of 10,10'-oxybisphenoxarsine to the solvent is in the range of about 0.083 to about 0.12, and b) the composition includes a plasticizer selected from the group consisting of diisononyl phthalate, diisodecyl phthalate, butylbenzyl phthalate, linear phthalate, and mixtures thereof.

7. A biocidal composition, which comprises:
a) about 0.5 to about 6 wt % 10, 10'-oxybisphenoxarsine,
b) about 5 to about 60 wt % of a castor oil based co-solvent selected from the group consisting of castor oil, alkoxylated castor oil having less than about 200 mols of alkoxyl per mol of glyceride, glyceryl ricinoleate, alkoxylated glyceryl ricinoleate having less than about 200 mols of alkoxyl per mol of glyceride, and mixtures thereof, and
c) about 34 to about 94 wt % of a plasticizer;
which composition includes less than about 10 grams per liter of VOC; and
which composition is a clear, homogeneous solution throughout the temperature range of about negative 13 to about 30 degrees Centigrade.

8. The composition of claim 7 which includes
a) about 1.5 to about 2.5 wt % 10, 10'-oxybisphenoxarsine,
b) about 15 to about 25 wt % of the castor oil based co-solvent, and
c) about 72 to about 82 wt % of the plasticizer.

9. The composition of claim 7 which includes
a) about 4.5 to about 5.5 wt % 10, 10'-oxybisphenoxarsine,
b) about 45 to about 55 wt % of the castor oil based co-solvent, and
c) about 39 to about 50 wt % of the plasticizer.

10. A biocidal composition for blending with a plastisol in a process for manufacturing a plastic material, which composition comprises:
10,10'-oxybisphenoxarsine in the amount of about 1.5 to about 5.5 wt %, and
a mixture of triglycerides of fatty acids including esterified ricinoleic acid, in which the esterified ricinoleic acid content of the triglycerides mixture is about 90 wt % of the total esterified fatty acid content of the triglycerides mixture;
which composition includes less than about 10 grams per liter of VOC; and
which composition is a clear, homogeneous solution throughout the temperature range of about negative 13 to about 30 degrees Centigrade.

11. A biocidal composition for blending with a plastisol in a process for manufacturing a plastic material, which composition comprises:
about 1.5 to about 5.5 wt % 10,10'-oxybisphenoxarsine, and
an alkoxylated castor oil, in which the alkoxylated castor oil has less than about 200 mols of alkoxyl per mol of glyceride and includes a mixture of ricinoleic acid esters of alkoxylated glycerol;
which composition includes less than about 10 grams per liter of VOC; and
which composition is a clear, homogeneous solution throughout the temperature range of about negative 13 to about 30 degrees Centigrade.

12. A biocidal composition for blending with a plastisol in a process for manufacturing a plastic material, which composition comprises:
about 1.5 to about 5.5 wt % 10, 10'-oxybisphenoxarsine, and
glyceryl ricinoleate;
which composition includes less than about 10 grams per liter of VOC; and
which composition is a clear, homogeneous solution throughout the temperature range of about negative 13 to about 30 degrees Centigrade.

* * * * *